US008454938B2

(12) United States Patent
Green et al.

(10) Patent No.: US 8,454,938 B2
(45) Date of Patent: Jun. 4, 2013

(54) TREATMENT OF RESPIRATORY DISEASES

(75) Inventors: Francis H. Y. Green, Calgary (CA);
Tamer Y. El Mays, Calgary (CA);
Samuel Schurch, Calgary (CA)

(73) Assignee: Solaeromed Inc., Calgary (CA)

( * ) Notice: Subject to any disclaimer, the term of this patent is extended or adjusted under 35 U.S.C. 154(b) by 1029 days.

(21) Appl. No.: 11/614,831

(22) Filed: Dec. 21, 2006

(65) Prior Publication Data

US 2007/0190183 A1    Aug. 16, 2007

Related U.S. Application Data

(60) Provisional application No. 60/597,841, filed on Dec. 21, 2005.

(51) Int. Cl.
*A61K 9/12* (2006.01)
*A61K 33/00* (2006.01)
*A61M 15/00* (2006.01)

(52) U.S. Cl.
USPC ............ 424/45; 128/204.18; 128/203.12; 514/826

(58) Field of Classification Search
USPC ............ 424/45; 128/204.18, 203.12; 514/826
See application file for complete search history.

(56) References Cited

U.S. PATENT DOCUMENTS

| | | | |
|---|---|---|---|
| 5,470,885 A | 11/1995 | Fuhrman et al. | |
| 5,490,498 A | 2/1996 | Faithfull et al. | |
| 5,531,219 A * | 7/1996 | Rosenberg | 128/203.12 |
| 5,770,585 A | 6/1998 | Kaufman et al. | |
| 5,773,024 A | 6/1998 | Unger et al. | |
| 5,853,003 A | 12/1998 | Faithfull et al. | |
| 5,873,359 A | 2/1999 | Zapol et al. | |
| 6,001,332 A | 12/1999 | Garrett | |
| 6,242,472 B1 | 6/2001 | Sekins et al. | |
| 6,411,852 B1 | 6/2002 | Danek et al. | |
| 6,432,384 B2 | 8/2002 | Albrecht | |
| 6,455,028 B1 | 9/2002 | Wulffhart et al. | |
| 6,677,322 B2 | 1/2004 | Sequeira et al. | |
| 6,679,859 B1 | 1/2004 | Keipert et al. | |
| 6,878,751 B1 | 4/2005 | Donnelly et al. | |
| 6,930,125 B2 | 8/2005 | Hunt et al. | |
| 2002/0010218 A1 | 1/2002 | Albrecht | |
| 2004/0127425 A1 | 7/2004 | Nudler et al. | |

FOREIGN PATENT DOCUMENTS

| | | |
|---|---|---|
| EP | 0727219 | 8/1996 |
| WO | WO 0209731 | 2/2002 |
| WO | WO 03/047603 A2 | 6/2003 |
| WO | WO 2004/026345 A1 | 4/2004 |
| WO | WO 2007/071052 A1 | 6/2007 |

OTHER PUBLICATIONS

Lehmler et al, CHEMTEC, vol. 29, No. 10, 7-12. XP-002494765, Liquid ventilation—A new way to deliver drugs to diseased lungs?*

(Continued)

*Primary Examiner* — Mina Haghighatian
(74) *Attorney, Agent, or Firm* — Bennett Jones LLP

(57) ABSTRACT

A method for treating a mammal suffering from a respiratory disease characterized by acute intermittent or chronic obstruction of the airways of the lungs, such as asthma, acute asthma, chronic obstructive pulmonary disease (COPD) and bronchiectasis comprising delivering to the lungs of the mammal a perfluorocarbon and a gas mixture comprising carbon dioxide ($CO_2$), and pharmaceutical compositions of $CO_2$ and perfluorocarbons are provided. The acute relief of airway obstruction provided by the said treatment provides an opportunity for concomitant or subsequent delivery of additional suitable active agent of conventional treatments.

26 Claims, 12 Drawing Sheets

OTHER PUBLICATIONS

Petit, J. M. and Boccar, M. (1967). Bronchodilator effect of CO2 during asthmatic paroxysms accompanied by respiratory alkalosis and ventilation perfusion disturbances. Arch. Int. Physiol., 75: 532-534.

Tashkin, D. P. and Simmons, D. H. (1972). Effect of Carbon Dioxide Breathing on Specific Airway Conductance in Normal and Asthmatic Subjects. Am. Rev. Resp. Disease, 106: 729-739.

Fisher, H. K. and Hansen, T. A. (1976). Site of Action of Inhaled 6 Per Cent Carbon Dioxide in the Lungs of Asthmatic Subjects before and after Exercise. Am. Rev. Resp. Disease, 114: 861-870.

Molony, V., Graf, W. and Scheid, P. (1976). Effects of CO2 on Pulmonary Air Flow Resistance in the Duck. Resp. Physiol., 26: 333-349.

Rodrigo, G., Rodrigo, C. and Hall, J. (2004). Acute asthma in adults: A review. Chest, 125: 1081-1102.

Hamelmann et al. (1997). Noninvasive measurement of airway responsiveness in allergic mice using barometric plethysmography. Am. J. Respir. Crit. Care Med. Sep. 1977, 156 (3 Pt 1): 766-775.

Von der Hardt et al., "Comparison of aerosol therapy with different perfluorocarbons in surfactant-depleted animals", Crit Care Med May 2004; 32(5):1200-6 (Abstract).

Al-Delaimy et al. (2001), The effects of carbon dioxide on exerices-induced asthma: an unlikely explanation for the effects of Buteyko breathing training, Med. J. Aust. 174(2), 72-74.

Dhuper, et al. (2003), Profile of near-fatal asthma in an inner-city hospital, Chest 124, 1880-1884.

Laffey and Kavanagh (1999) Carbon dioxide and the critically ill—too little of a good thing? The Lancet, 354, 1283-1286.

Mutlu et al. (2002), Severe status asthamaticus: management with permissive hypercapnia and inhalation anesthesia, Crit Care Med 30(2), 477-480.

Ansel et al., Pharmaceutical Dosage Forms and Drug Delivery Systems, Sixth Edition, (Malvern Pa.: Lea & Febiger, 1995), Chapter 13—Aerosols, Inhalations, and Sprays, 443-459.

Brocklebank, D. and Wright, J., Systemic review of clinical effectiveness of pressurised metered dose inhalers versus other hand held inhaler devices for delivering corticosteroids in asthma, (2001) BMJ 323: 896-904.

Schürch S. Perfluorocarbon-Surfactant Interactions: Biophysical Aspects, 5th European Symposium on Perfluorocarbon Application and Liquid Ventilation, Milan, Italy, Mar. 17-18, 2006.

Schürch S, Bachofen H, Possmayer F. Surface activity in situ, in vivo, and in the captive bubble surfactometer. Comp Biochem Physiol A Mol Integr Physiol. May 2001;129(1):195-207. Review.

Wolfson MR, Shaffer TH. Pulmonary applications of perfluorochemical liquids: ventilation and beyond. Paediatr Respir Rev. Jun. 2005; 6(2):117-27. Review.

El Mays T., Schürch S., Koetzler R., Green F.H.Y.. Treatment of Experimental Asthma with Surfactant-Perfluorocarbon Aerosols. European Journal of Medical Research, vol. 11/Supplement I, p. 4, Mar. 16, 2006.

El Mays T, Wilson R, Poulin M, Whitelaw W, Hollenberg M, Green F. Evaluation of the scientific basis of the Buteyko Breathing Technique for the treatment of asthma. Abstract. Can Respir J vol. 11 No. 3 Apr. 2004, p. 234.

Demeter SL, Cordasco EM. Hyperventilation syndrome and asthma. Am J Med. Dec. 1986;81(6):989-94.

Han, JN., Hu, Z., Zhu, YJ., Van den Bergh, O., & Van de Woestijne, KP. The complaints in patients with asthma are compounded by hyperventilation [abstract]. Am J Respir Crit Care Med; 159: A788. 1999.

Lindeman KS, Croxton TL, Lande B, Hirshman CA. Hypocapnia-induced contraction of porcine airway smooth muscle. Eur Respir J. Nov. 1998;12(5):1046-52.

Varani J, Hirsch RB, Dame M, Johnson K. Perfluorocarbon protects lung epithelial cells from neutrophil-mediated injury in an in vitro model of liquid ventilation therapy. Shock; 6(5):339-44. Nov. 1996.

Rotta AT, Gunnarsson B, Fuhrman BP, Wiryawan B, Hernan LJ, Steinhorn DM. Perfluorooctyl bromide (perflubron) attenuates oxidative injury to biological and nonbiological systems. Pediatr Crit Care Med. Apr. 2003;4(2):233-8.

Mrozek JD, Smith KM, Bing DR, Meyers PA, Simonton SC, Connell JE, Mammel MC. Exogenous surfactant and partial liquid ventilation: physiologic and pathologic effects. Am J Respir Crit Care Med 156:1058-1065, 1997.

Shashikant BN, Miller TL, Jeng MJ, Davis J, Shaffer TH, Wolfson MR. Differential impact of perfluorochemical physical properties on the physiologic, histologic, and inflammatory profile in acute lung injury. Crit Care Med. May 2005;33 (5):1096-103.

Schürch S, Amato M, Valls-i-Soler A., Green F H Y. Surface properties of surfactant-perfluorocarbon combinations related to partial and total liquid ventilation. 15th International Workshop on Surfactant Replacement, Kos, Jun. 2-3, 2000, Biol Neonate 2000; 77 (suppl 1) p. 25.

Feng W, Garrel H, Speert DP, King M. Improved clearability of cystic fibrosis sputum with dextran treatment in vivo. Amer J Resp Crit Care Med 157:710-714, 1996.

Corcoran TE, Gamard S. Development of aerosol drug delivery with helium oxygen gas mixtures. J Aerosol Med. 2004 Winter;17(4)299-309. Review.

\* cited by examiner

TREATMENT OF RESPIRATORY DISEASES

FIELD OF THE INVENTION

The invention relates to the treatment of respiratory diseases. More particularly, the invention relates to the treatment of patients suffering from respiratory diseases characterized by acute, intermittent or chronic obstruction of the airways of the lungs by administering a therapeutically effective amount of (a) a perfluorocarbon, and (b) carbon dioxide ($CO_2$) gas either separately, sequentially or as a mixture.

BACKGROUND OF THE INVENTION

Respiratory diseases such as asthma and other chronic obstructive pulmonary diseases (COPD) are characterized by the constriction or narrowing of the airways of the lungs. Asthma is a chronic disease in which sufferers have repeated attacks of difficulty in breathing and coughing. The prevalence and severity of asthma, as well as its associated mortality, have increased in the last few decades. In the United States, 40 million people have asthma and they account for 3 million emergency department visits, 500,000 hospitalizations, and nearly 6,000 deaths annually [see Rodrigo, G., Rodrigo, C. and Hall, J. (2004) *Acute asthma in adults: a review*. Chest 125: 1081-1102].

The majority of asthmatics (90-95%) suffer from the mild to moderate form of the disease and can control the disease with appropriate treatment. However, the 5-10% of asthmatics that suffer from the severe form of the disease, also known as severe persistent or acute severe asthma, are faced with frequent and life-threatening attacks. During an acute asthma attack, the airways (e.g., bronchi and bronchioles) are greatly narrowed by swelling (caused by inflammation of the inner lining of the bronchi/bronchioles), bronchoconstriction (caused by contraction of the bronchi/bronchioles smooth muscles) and mucus plugging (caused by the excess production of mucus produced by mucous gland secretions and cells lining the airway wall). The resultant narrowed airways make it more difficult for air to pass through to adequately ventilate the air sacs in the lungs, resulting in reduction of oxygen (hypoxaemia) in the blood and reduced oxygen supply to vital organs.

An important first step for treatment during an acute asthma attack is to reduce swelling, relax the muscles of the airways and loosen mucous plugs, thus opening the airways and making it easier to breathe. In addition, once the airways have been opened, administration of conventional therapeutics such as beta-2-agonists, anticholinergics and anti-inflammatory agents such as glucocorticosteroids will be more efficient as these drugs will be able to reach their active site more effectively.

COPD is a slowly progressive disease of the airways that is characterized by the gradual loss of lung function. Patients with COPD often require emergency treatment and sometimes hospitalizations during periods of exacerbations of their disease. COPD leads to chronic airflow obstruction, which is defined as a persistent decrease in the rate of airflow through the lungs when the person breathes out (exhales). Symptoms such as wheezing and shortness of breath are relieved when airflow obstruction decreases by reversing bronchial smooth muscle spasm, inflammation, and increased secretions.

Cystic fibrosis is an example of an obstructive lung disorder that results in bronchiectasis and progressive declines in FEV1. In this disease, there is a genetic defect in the transport of chloride or chlorine across the airway lining (epithelial) cells. This results in a reduced water content in the mucous blanket with increased viscosity of the mucus. The abnormal mucus becomes infected, which results in destruction and fibrosis of the bronchial wall. The mucous plugs and inflammation cause airway obstruction. Even with optimal treatment, most affected individuals die in their third or fourth decades.

The present invention is useful, for example, during acute asthma attacks as it provides potent and rapid bronchial relaxation so that both air and, if necessary, medication can be more effectively delivered to the lungs. Further, the present invention is useful for treating any respiratory disease where the airways are narrowed due to inflammation of the airways or constricted due to airway smooth muscle contractions (bronchoconstriction) and have mucous plugs such as are found in asthma, COPD and other obstructive lung diseases, such as bronchiectasis.

SUMMARY OF THE INVENTION

The present invention features methods for the treatment of a patient suffering from a respiratory disease characterized by acute, intermittent or chronic obstruction of the airways of the lungs. It involves administering to the lungs of the patient therapeutically effective amounts of perfluorocarbon and carbon dioxide ($CO_2$), either separately, sequentially or as a mixture.

It was discovered that $CO_2$ is a potent bronchial relaxant capable of opening up constricted airways within a short period of time after breathing in a gas mixture containing at least about 2% by volume $CO_2$. Further, it was discovered that delivery of perfluorocarbon (either as a gas or an aerosol) also acts as an independent bronchial relaxant. The individual action of each of these broncho-relaxants, however, is relatively short lived.

Surprisingly, it was discovered that the combination of $CO_2$ and perfluorocarbon, for example, perfluorotributylamine (FC-43), FC-77 (also known as Fluorinert™), perfluorodecalin, perfluorooctylbromide, and the like, resulted in a greater than additive relaxant effect when compared to values obtained when each compound was used alone. Further, the relaxant effect of the combination of perfluorocarbon and $CO_2$ was prolonged over a greater period of time than was found for the individual components separately delivered.

Without being bound to theory, it is thought that these beneficial effects are likely due in part to the ability of perfluorocarbon, such as FC-43, FC-77, perfluorodecalin, perfluorooctylbromide, and the like, to dissolve very large quantities of gases, such as $CO_2$, thereby providing a sustained release of $CO_2$ from perfluorocarbon in the airways. In addition, the ability of perfluorocarbon to reduce the surface tension in inflamed and constricted airways due to the low interfacial tension of the perfluorocarbon-lung surfactant interface may also contribute to the prolonged effect of the mixture of the present invention. This may result in an additional benefit of lowering surface tension in the inflamed airways and loosening mucus plugs.

Thus, in one aspect, the present invention relates to a treatment of a mammal suffering from a respiratory disease characterized by acute, intermittent or chronic obstruction of the airways of the lungs involving delivering to the lungs of the mammal a therapeutically effective amount of a combination of a perfluorocarbon and $CO_2$ mixed with a gas (hereinafter referred to as "$CO_2$-containing gas mixture"). In one embodiment, the therapeutically effective amount of the combination is an amount which when delivered to the lungs results in bronchodilation.

In one embodiment, the concentration of $CO_2$ in the $CO_2$-containing gas mixture is between about 2% by volume to about 20% per volume. In another embodiment, the concentration of $CO_2$ in the $CO_2$-containing gas mixture is such that when the combination of perfluorocarbon and $CO_2$-containing gas mixture is delivered to a patient's lungs, the concentration of $CO_2$ in the lungs is at least about 2%, preferably at least about 2% to about 20%, of the total lung capacity, wherein the total lung capacity comprises the fluid volume of the lung when fully inflated during normal breathing. In another embodiment, the concentration of perfluorocarbon is such that when the combination of perfluorocarbon and $CO_2$-containing gas mixture is delivered to the lungs the concentration of perfluorocarbon in an individual patient's lungs when the lungs are fully inflated during normal breathing is between about 1 mg/liter and about 500 mg/liter. In one embodiment, the combination of perfluorocarbon and $CO_2$-containing gas mixture is delivered to the lungs as an aerosol, for example, a perfluorocarbon aerosol driven by a gas mixture containing $CO_2$.

In a further aspect, the invention relates to a treatment of a mammal suffering from a respiratory disease characterized by acute, intermittent or chronic obstruction of the airways of the lungs involving delivering to the lungs of the mammal a therapeutically effective amount of a mixture of $CO_2$ dissolved in a perfluorocarbon. The $CO_2$/perfluorocarbon mixture can then be administered to the lungs as an aerosol, gas or liquid bolus. In one embodiment, the therapeutically effective amount of the mixture is an amount which when delivered to the lungs results in bronchodilation.

In one embodiment, the respiratory disease is asthma. In another embodiment, the respiratory disease is COPD. In yet another embodiment, the respiratory disease is an acute asthma attack. In another embodiment, the respiratory disease is bronchiectasis.

In another aspect, the invention relates to a treatment of a mammal suffering from a respiratory disease characterized by acute, intermittent or chronic obstruction of the airways of the lungs involving separately delivering to the lungs of the mammal (1) a therapeutically effective amount of a perfluorocarbon and (2) a gas mixture having a therapeutically effective amount of $CO_2$. In one embodiment, the perfluorocarbon is delivered separately in an aerosolized form followed by the delivery of the gas mixture having $CO_2$.

In another aspect, the invention relates to a treatment of a mammal suffering from a respiratory disease characterized by acute, intermittent or chronic obstruction of the airways of the lungs involving first delivering to the lungs a therapeutically effective amount of a combination of a perfluorocarbon and a $CO_2$-containing gas mixture to open up the airways, followed by delivering to the lungs a therapeutically effective amount of an additional suitable active agent. In one embodiment, the active agent is either an anti-inflammatory drug, such as corticosteroid, cromolyn sodium or a leukotriene antagonist, or a bronchodilator, such as theophylline and its derivatives, beta-adrenergic agonists, anticholinergics and therapeutic pulmonary surfactant.

In another aspect, the invention relates to a treatment of a mammal suffering from a respiratory disease characterized by acute, intermittent or chronic obstruction of the airways of the lungs involving (1) delivering to the lungs of the mammal a therapeutically effective amount of a perfluorocarbon, (2) delivering to the lungs a gas mixture having a therapeutically effective amount of $CO_2$, and (3) delivering to the lungs a therapeutically effective amount of an additional suitable active agent.

The invention also relates to specific pharmaceutical compositions including a perfluorocarbon and $CO_2$, preferably, a $CO_2$-containing gas mixture. Preferably, perfluorocarbons having a high solubility for $CO_2$ are used in the pharmaceutical compositions. Without being limited, examples of suitable perfluorocarbons include perfluoro-alkanes, perfluoro-ethers, and perfluoro amines, or more specifically perfluorodecalin, perfluorohexane, octafluoropropane, perfluoroperhydrophenanthrene, perfluorobutane, perfluorooctane, perfluoromethyldecalin, perfluorocarbons containing bromide such as perfluorooctylbromide, perfluorodecalin, perfluorooctylethane, bis(perfluorobutyl)ethane or using the trade names, such as FC-43, FC-40, FC-5312, FC-77, FC-75 (3M Co), Rimar 101 (Mitsubishi, Milan) and Caroxin.

The pharmaceutical compositions of the present invention act to increase the relaxant effect of $CO_2$ and to loosen mucus plugs. Preferably, the perfluorocarbons of the present invention are compatible with the airway surfactant that coats the airways. Thus, the compositions of the present invention rapidly open up closed airways and the perfluorocarbon spreads along the airways facilitating further opening and loosening of mucous plugs.

In one embodiment, the $CO_2$-containing gas mixture has a concentration of $CO_2$ of about 2% by volume to about 20% by volume. In another embodiment, the $CO_2$-containing gas mixture has a concentration of $CO_2$ such that when the combination of perfluorocarbon and $CO_2$-containing gas mixture is delivered to a patient's lungs, the concentration of $CO_2$ in the lungs is at least about 2%, preferably at least about 2% to about 20%, of the total lung capacity, wherein the total lung capacity comprises the fluid volume of the lung when fully inflated during normal breathing.

In another embodiment, the $CO_2$-containing gas mixture further has oxygen and/or other low viscosity gases such as helium present. In one embodiment, the $CO_2$-containing gas mixture has an $O_2$ concentration of about 21% by volume to about 80% by volume. In another embodiment, the amount of oxygen in the $CO_2$-containing gas mixture is between about 15% by volume to about 21% by volume, to give a $CO_2$-containing gas mixture that is hypoxic.

In another embodiment, the $CO_2$-containing gas mixture comprises between about 2% to about 20% $CO_2$ by volume, 21% $O_2$ by volume and the remainder helium. When perfluorocarbons with relatively high vapour pressure at 37° C. are used, above approximately 40 Torr, these perfluorocarbons would be in the gaseous state upon aerosolization and likely behave like a helium-containing gas mixture, as the viscosity of the vaporized perfluorocarbons would likely also be very low. This is due to the weak intermolecular interaction forces, as seen by the low (below about 18 mN/m) surface tensions of these perfluorocarbon fluids.

The route of delivery of the pharmaceutical compositions of the invention is intrapulmonary and can be delivered to the lungs by any number of means known in the art. By way of example, a nebulizer connected to a compressor such as Pari LC-Jet Plus® nebulizer manufactured by Pari Respiratory Equipment, Inc., Richmond, Va., and connected to a compressed gas source could be used. For example, the nebulizer may be filled with perfluorocarbon and the compressed gas source filled with the $CO_2$-containing gas mixture. In the alternative, the nebulizer may be filled with perfluorocarbon and a suitable active agent, and the compressed gas source filled with the $CO_2$-containing gas mixture. In the alternative, the Pari e-Flow™ system could be used or any other suitable hand held nebulizer known to a person skilled in the art.

In the further alternative, a metered-dose inhaler could also be used. Metered-dose inhalers are described in Remington:

*The Science and Practice of Pharmacy*, Twentieth Edition (Easton, Pa.: Mack Publishing Co., 2000) and in Ansel et al., *Pharmaceutical Dosage Forms and Drug Delivery Systems*, Sixth Edition (Malvern, Pa.: Lea & Febiger, 1995). The clinical effectiveness of pressurized metered dose inhalers versus other hand held dose inhalers is discussed in Brocklebank, D. and Wright, J., (2001) BMJ 323: 896-904, incorporated herein by reference. The metered-dose inhaler would automatically dispense, in a puff intended for inhalation in a single or multiple breaths, a set amount of the pharmaceutical composition when activated by the patient in need of treatment.

In a further embodiment, the pharmaceutical compositions of the present invention may be a liquid composition comprising $CO_2$ dissolved in a perfluorocarbon liquid for delivery to the lungs in the form of a bolus by intratracheal installation. In another embodiment, the pharmaceutical compositions of the present invention may also be a gaseous or aerosol composition for inhalation through a mask or in a tent.

The pharmaceutical compositions of the present invention may be administered in conjunction with other longer acting bronchodilators known in the art. For example, upon the onset of an acute asthma attack, the pharmaceutical composition of the present invention may be administered first to rapidly relax and open the airways. Shortly thereafter, or as soon as the patient feels some relief, the patient then delivers a beta-2-agonist bronchodilator such as salbutamol (e.g., Ventolin™, Volmax™) and terbutaline (Bricanyl™), also by means of a nebulizer or metered dose inhaler. Alternatively, beta-2-agonists and/or corticosteroids could be incorporated directly into the pharmaceutical compositions, possibly in sequence using one delivery system.

In another embodiment, the pharmaceutical compositions may be delivered by means of an inhaler device, such as a hand-held nebulizer, having two chambers, where one chamber contains perfluorocarbon and the other chamber contains a $CO_2$-containing gas mixture, and a mechanism for releasing the perfluorocarbon and the $CO_2$-containing gas mixture to the lungs. In one embodiment, the releasing mechanism releases the perfluorocarbon and the $CO_2$-containing gas mixture simultaneously to create a fine droplet aerosol of perfluorocarbon particles in the gas mixture. In another embodiment, the releasing mechanism releases the perfluorocarbon and the $CO_2$-containing gas mixture sequentially. In yet another embodiment, the inhaler device further comprises a third chamber containing additional suitable active ingredients such as an anti-inflammatory drug or bronchodilator or both.

It is understood that the perfluorocarbon and the $CO_2$-containing gas mixture could be delivered separately and sequentially by a number of methods known in the art. By way of example, but not meant to be limiting, the perfluorocarbon could first be delivered to a patient as a liquid bolus, followed by delivering the $CO_2$-containing gas mixture by means of a face mask or ventilation tent, or followed by delivering PFC aerosol and the $CO_2$-containing gas mixture by means of a face mask or ventilation tent. Thus, in one aspect, the present invention relates to a method for treating a mammal suffering from a respiratory disease characterized by acute intermittent or chronic obstruction of the airways of the lungs, comprising separately delivering to the lungs of the mammal a therapeutically effective amount of a perfluorocarbon and a gas mixture having a therapeutically effective amount of $CO_2$.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION

Figure 1A:
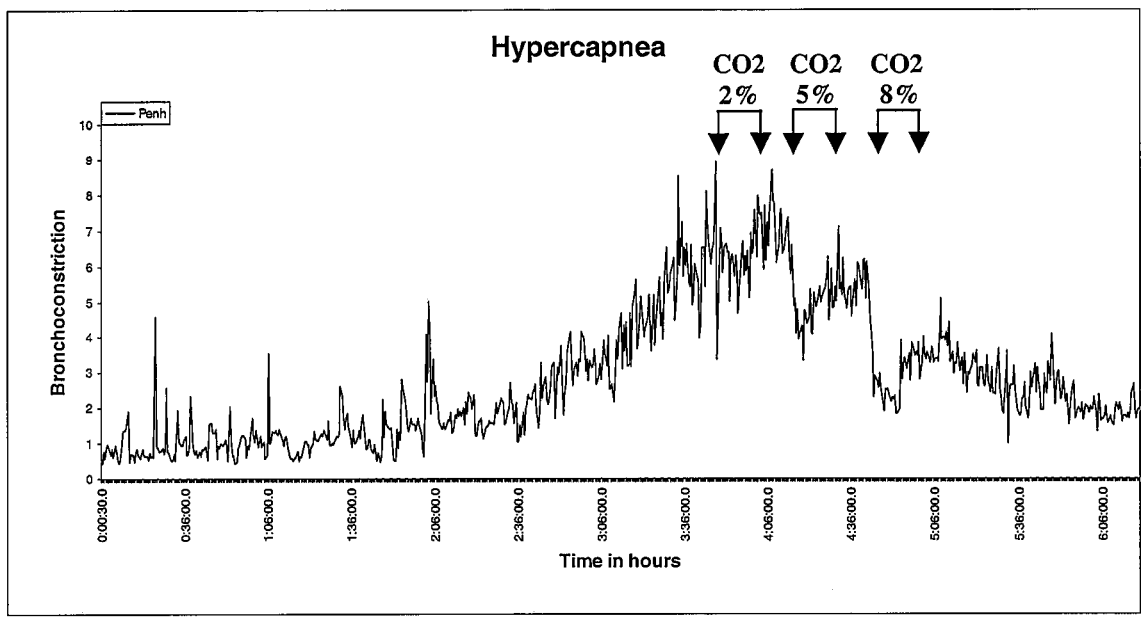
FIG. 1a is a graph showing the effects of inhaling various concentrations of carbon dioxide (2%, 5% and 8%) on allergic bronchoconstriction in a Brown Norway rat.

The invention is a convenient yet highly effective method of treating a patient suffering from a respiratory disease characterized by acute, intermittent or chronic obstruction of the airways of the lungs, such as asthma, acute asthma, COPD and bronchiectasis. For example, the present invention is particularly effective in opening up the airways of patients suffering from an acute asthma attack. The present invention represents a significant advantage over conventional bronchodilators because of the immediate or fast acting effect of the novel mixture.

Further, the invention has improved penetration of constricted airways because it includes $CO_2$, either as a gas mixture or alone, and a perfluorocarbon (in liquid and/or vapour phases) that preferably has a high solubility for $CO_2$ and interfacial properties that facilitates spread along constricted airways. Various modifications (e.g., a metered dose inhaler) of the present invention could also be used for routine treatment of chronic airway obstruction, for example, in patients suffering from asthma and COPD, and compositions (e.g., a fluid bolus) could be developed that would be of use in the emergency room or by emergency medical services for the treatment of the severely ill patient, for example, a patient having an acute asthma attack.

A "combination of perfluorocarbon and $CO_2$-containing gas mixture" of the present invention is said to be "therapeutically effective" in a given patient if:

(1) airway obstruction is reduced (i.e., bronchodilation or airway relaxation) by reducing airway constriction by at least between 5 and 30% within about 30 seconds to about 15 minutes after delivery of the perfluorocarbon and the $CO_2$-containing gas mixture, delivered either separately or as a mixture; or (2) airway relaxation continues for at least 5 minutes after delivery of the perfluorocarbon and $CO_2$-containing gas mixture, delivered either separately, sequentially or as a mixture.

By the terms "effective amount" or "therapeutically effective amount" of a pharmaceutical composition of the present invention or an additional suitable active agent are meant a non-toxic but sufficient amount of the composition or active agent to provide the desired therapeutic effect. The exact amount of the composition or active agent to be delivered to a subject to provide the desired effect will vary from subject to subject, depending on the age, weight, and severity of the airway constriction.

By the term "therapeutically effective amount of $CO_2$" is meant a suitable concentration of $CO_2$ which when inhaled by a patient will result in a concentration of $CO_2$ in the lungs of at least about 2%, preferably at least about 2% to about 20%, of the patient's total lung capacity, wherein the total lung capacity comprises the fluid volume of the lung when fully inflated during normal breathing.

By the term "therapeutically effective amount of perfluorocarbon" is meant a suitable concentration of perfluorocarbon which when inhaled by a patient will result in a concentration of perfluorocarbon (aerosol plus vapour phase) in the patient's lungs when the lungs are fully inflated during normal breathing of between about 1 mg/liter and about 500 mg/liter.

It is understood that the pharmaceutical compositions of the present invention may comprise a mixture of two, three, four or more compatible perfluorocarbons. The $CO_2$ concentration in the pharmaceutical compositions is such that the concentration of $CO_2$ is at least about 2% to about 20% of a patient's total lung capacity, wherein the total lung capacity comprises the fluid volume of the lung when fully inflated during normal breathing, when the pharmaceutical composition is administered to the patient's lungs. The concentration of perfluorocarbon in the pharmaceutical compositions is such that when the pharmaceutical composition is delivered to the patient's lungs the concentration of perfluorocarbon (aerosol plus vapour phase) in the patient's lungs when the lungs are fully inflated during normal breathing is between about 1 mg PFC/liter and about 500 mg PFC/liter.

Oxygen may also be present in the pharmaceutical compositions of the invention in amounts such that the concentration of $O_2$ is at least about 15% to about 80% of a patient's total lung capacity, wherein the total lung capacity comprises the fluid volume of the lung when fully inflated during normal breathing, when the pharmaceutical composition is administered to the patient's lungs. The compositions may have one or more pharmaceutically acceptable excipients in addition to the active ingredients.

The following examples are meant to illustrate, not limit, the invention.

EXPERIMENTAL INFORMATION

Animals:

Pathogen-free Brown Norway rats BN/SsNHsd weighing 150-199 g were purchased from Harlan. Rats were housed in plastic cages in the University of Calgary Health Sciences Animal Resources Centre. Rats had access to water and rodent laboratory chow (Prolab® RMH 2500 5P14) with a 12 hr light/dark cycle maintained. All procedures involving animals were approved by the Animal Care Committee.

Drug Sources:

Ovalbumin (OVA), pertussis toxin were purchased from Sigma-Aldrich, Canada. $Al(OH)_3$ was purchased from Fisher Scientific Canada. Tanks containing a gas mixture of air and carbon dioxide (2, 5, 8, 10 and 20% by volume in air) were purchased from Praxair® Canada. Other chemicals and reagents were from standard commercial sources. PFCs were purchased from 3M Company and F2 Chemicals.

Equipment:

A whole body plethysmograph/chamber from Buxco®) was purchased from Buxco®. A dual-chamber jet nebulizer was provided by Arcotech AG, Aarburg, Switzerland.

Experimental Protocol:

An animal model of allergic asthma was developed by sensitizing Brown Norway rats (BNR) to ovalbumin (OVA) and subsequently challenging them with the same allergen.

(a) Brown Norway Rats Sensitization:

Male Brown Norway rats (BN/SsdNhsd) 150-199 g were used. A stock solution prepared containing the following ingredients: 10 mL 0.9% of sterile saline solution, 100 µL of ovalbumin solution 1 mg/mL in saline, 1.5 g $Al(OH)_3$ and 10 µL *Bordetella Pertussis* purified toxin stock solution 500 ng/mL. The solution is mixed thoroughly but not vortexed and then injected intraperitoneally into each rat using a 1 cc syringe and 25-gauge needle.

(b) Brown Norway Rat Ovalbumin Challenge:

The rat is placed in the whole body plethysmograph/chamber for approximately 30 minutes in order to calm down. Baseline pulmonary function is recorded for 30 minutes. A solution of ovalbumin 5% in saline is aerosolized for 5 minutes using an ultrasonic nebulizer from Buxco®. The pulmonary function is recorded for 6 hrs during which the effects of different treatments on airway resistance were evaluated.

(c) Whole Body Plethysmography:

A whole body plethysmograph from Buxco® was used to monitor pulmonary function and the effect of perfluorocarbon fluids (PFCs) and/or different gas mixture containing $CO_2$ on constricted airways. The plethysmograph consists of a chamber with a pressure transducer along with humidity and temperature probes connected to an amplifier Max II, which is connected to a personal computer and managed by BioSystem XA software. In addition, there are two flow regulators to pump the air or $CO_2$ containing gas mixture in and out of the chamber, and an ultrasonic nebulizer. The primary advantage of the Buxco® methodology is that it is non-invasive and minimizes stress, with animals allowed to freely roam within the measuring chamber. The evaluation of bronchoconstriction was achieved using the Penh (enhanced pause) (an index of airway obstruction) [see Hamelmann et al., (1997) Noninvasive measurement of airway responsiveness in allergic mice using barometric plethysmography, *Am J Respir Crit Care Med* 1977 September; 156(3 Pt 1):766-775, incorporated herein by reference].

(d) Perfluorocarbon Delivery:

Perfluorocarbon was delivered using a dual-chamber jet nebulizer (Arcotech AG, Aarburg, Switzerland) driven by pumped air or a $CO_2$ containing gas mixture.

(e) Determination of PFC Concentration and Particle Size in the Exposure System:

PFC aerosols were generated by Arcotech dual-chamber jet nebulizer. The particles were captured on an eight-stage cascade impactor. The methods used to assess particle size were based on those methods described in European Standard EN13544-1 (EN13544-1: 2000 Respiratory Therapy Equipment-Part 1: Nebulizing Systems and their Components, incorporated hereto by reference).

The concentration particle size of nebulised PFC was determined using the following steps:
1. The flow rate (liter per minute) was determined by connecting the Arcotech nebulizer to a flow meter.
2. PFC in the nebulizer was weighed before and after being nebulized for 3 minutes to determine its weight loss. This was the total amount nebulized in mg.
3. The particulate (liquid droplets) output of the nebulizer was captured for 3 minutes on a pre-weighed impaction substrate (cut CF/A for Marple 298X impactor) and the weight difference on each impaction substrate determined to +/−0.01 mg. The particle size distribution, MMAD, and GSD were determined as defined in EN13544-1.
4. For each PFC, the difference between the weight of particulate PFC collected on a filter and the total weight of the PFC aerosolized (as described in step 2 above) constituted the amount of PFC in the vapor state.
5. Knowing the total volume and the weights, the PFC concentration (mg/liter) was calculated for the total PFC output, the aerosol (liquid droplets) component and for the PFC in vapor state.

EXAMPLE 1

Effect of Inhaling Various Concentrations of $CO_2$ on Bronchoconstricted Rats

A gas mixture containing air and $CO_2$ (2, 5, 8, 10 and 20%, respectively, by volume) was delivered to the plethysmograph chamber as described above. The gas was monitored ($O_2$ and $CO_2$) using a gas analyzer from Buxco® and pulmonary function was recorded during and after cessation of the treatment. All treatments were delivered during the late phase response to OVA challenge.

Figure 1B:
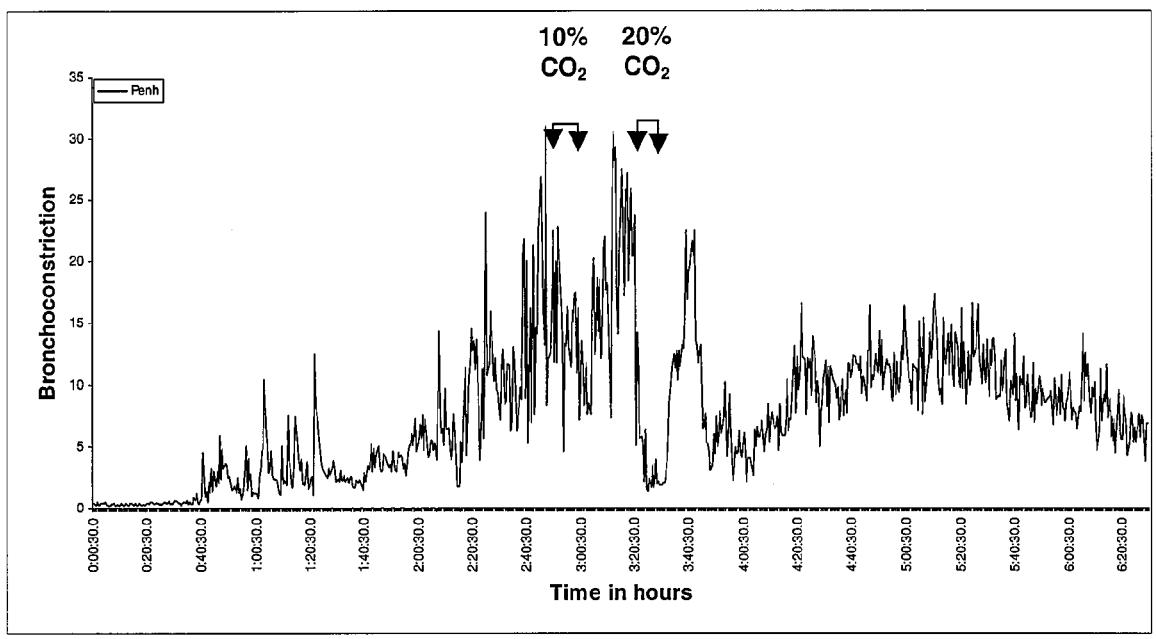
FIG. 1b is a graph showing the effects of inhaling various concentrations of carbon dioxide (10% and 20%) on allergic bronchoconstriction in a Brown Norway rat.

FIGS. 1a and 1b illustrate that $CO_2$ alone acts as a bronchodilator and that the opening of constricted airways is dose dependent. In these experiments, a gas mixture was used comprising 2%, 5%, and 8% $CO_2$ by volume (FIG. 1a) and 10% and 20% (FIG. 1b) $CO_2$ by volume, with the balance being air. The percent reduction of bronchoconstriction was measured as described above. Both FIGS. 1a and 1b show that increased bronchodilation was observed when increasing concentrations of $CO_2$ were administered.

Figure 1C:
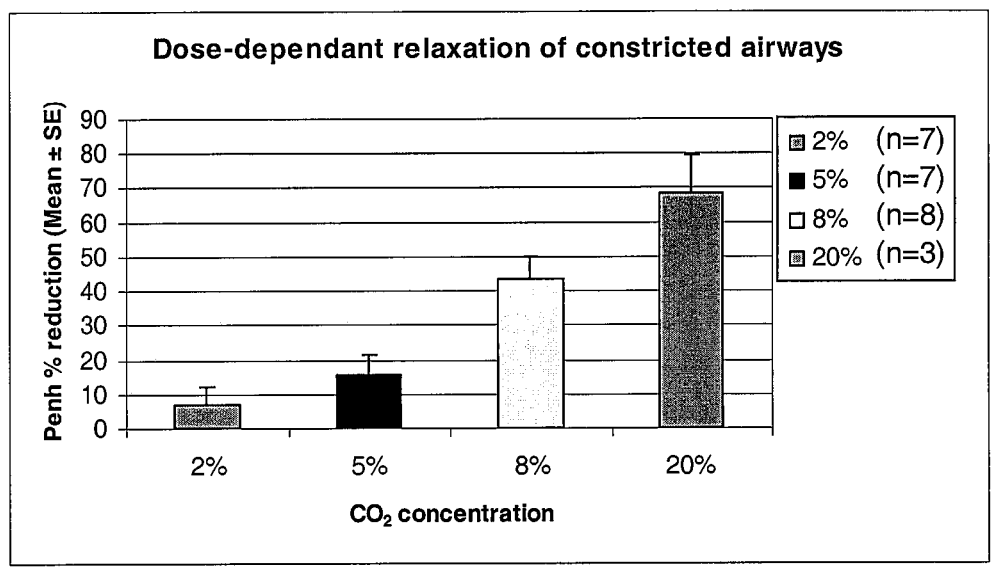
FIG. 1c is a bar graph showing reduction of airway constriction after inhalation of a gas mixture containing air and 2%, 5%, 8%, and 20% carbon dioxide by volume in groups of 3-8 bronchoconstricted rats.
Figure 2A:
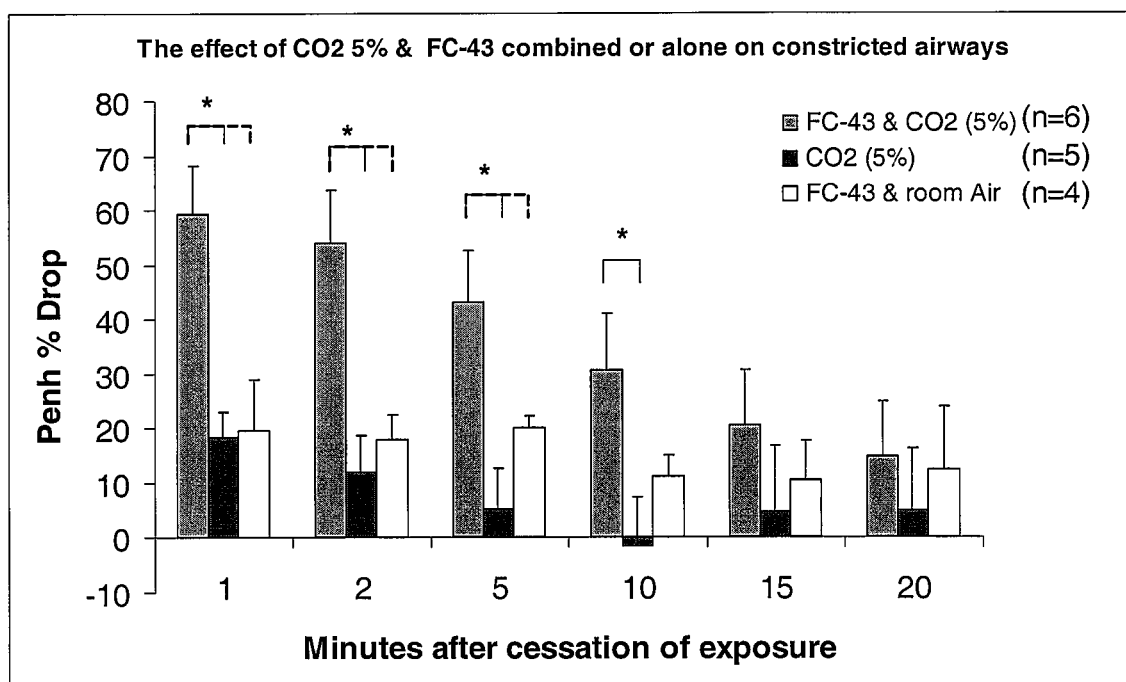
FIG. 2a is a bar graph showing reduction of airway constriction versus minutes after cessation of exposure to 5% carbon dioxide by volume in air, FC-43 in air, and a mixture of 5% carbon dioxide by volume in air and FC-43.
Figure 2B:
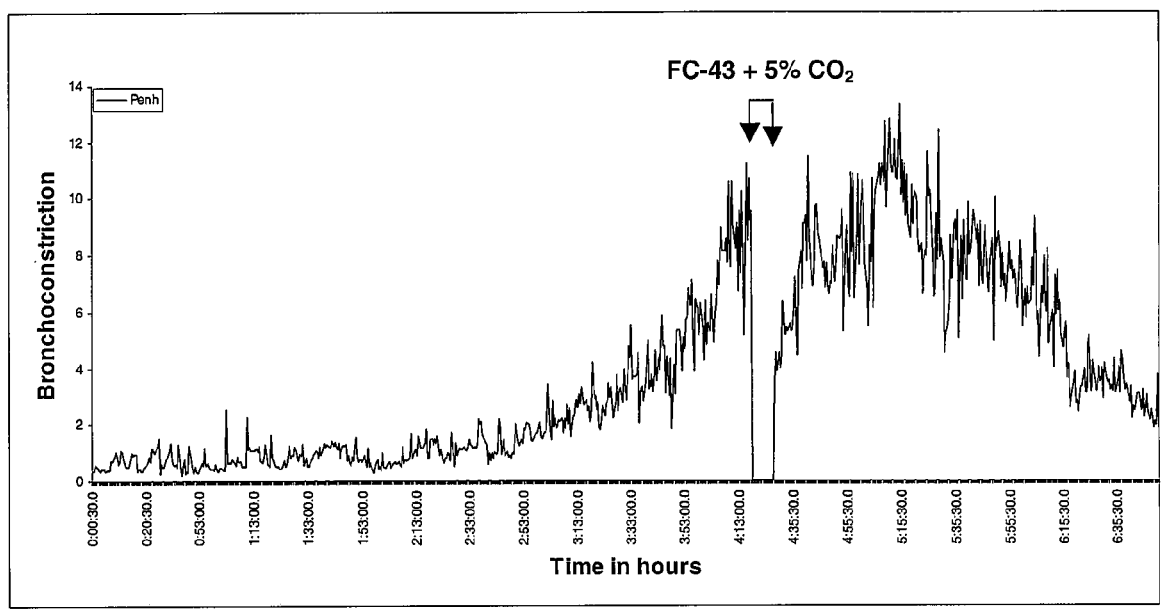
FIG. 2b is a graph showing the effects of inhaling a combination of FC-43 and 5% carbon dioxide on allergic bronchoconstriction in Brown Norway rats.
Figure 3:
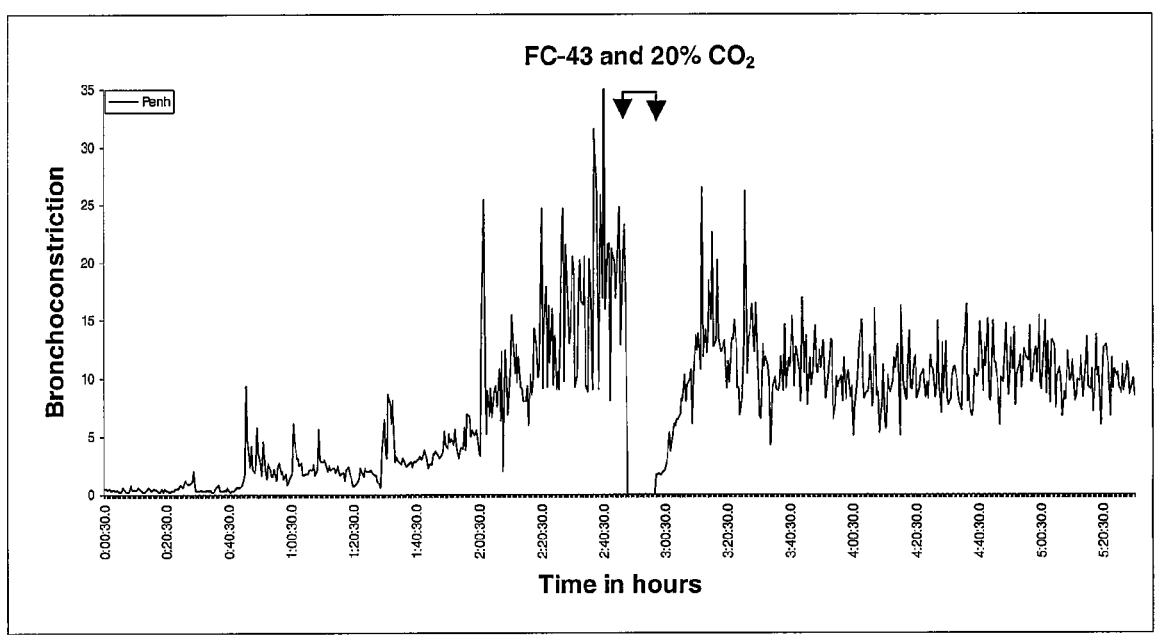
FIG. 3 is a graph showing the effects of inhaling a combination of FC-43 and 20% carbon dioxide on allergic bronchoconstriction in Brown Norway rats.

FIG. 1c is a bar graph showing the average values obtained with groups of 3-7 rats for dose-dependent relaxation of constricted airways with inhalation of a mixture of air and increasing amounts of $CO_2$ (2%, 5%, 8%, and 20% $CO_2$ by volume). Percent reduction of bronchoconstriction was measured as described above. The relaxation with both 20% and 8% $CO_2$ was significantly ($P<0.05$) higher than with both 2% and 5% and FIG. 1c further shows that the opening of constricted airways is dose dependent.

EXAMPLE 2

Effect of Inhaling a Combination of Perfluorocarbon and $CO_2$ on Bronchoconstriction in OVA Exposed Rats Compared to a $CO_2$/Air Mixture Alone or a Perfluorocarbon/Air Mixture Alone In this example, three different conditions were tested: (1) perfluorotributylamine (FC-43) plus 5% $CO_2$ in air, to give a final concentration of $CO_2$ in the mixture of 5% by volume and a FC-43 aerosol in the $CO_2$ mixture, when nebulized, of approximately 39 mg/liter, (2) an air mixture of 5% $CO_2$ by volume in air, and (3) an FC-43 aerosol in air, when nebulized, of 39 mg/liter. All treatments were delivered during the late phase response to OVA challenge.

The gas mixture containing air and 5% $CO_2$ by volume was delivered to the plethysmograph chamber as described above. Perfluorocarbon was delivered using the Arcotech dual chamber jet nebulizer driven by an air pump. For the perfluorocarbon (PF-43) and $CO_2$ in air combination, FC-43 was placed in the Arcotech dual chamber jet nebulizer and driven by the gas mixture containing air and 5% $CO_2$. For technical reasons in these experiments pulmonary function was evaluated immediately after cessation of the treatment.

Percent reduction of bronchoconstriction was measured as described above. FC-43 was chosen because it is compatible with the capacity of pulmonary surfactant films to achieve near zero minimum surface tensions upon film compression (equivalent to lung exhalation during respiration).

FIG. 2*a* is a bar graph showing that the FC-43 plus 5% by volume in air $CO_2$ mixture resulted in a significantly stronger and prolonged effect than with either FC-43 or 5% by volume in air $CO_2$ alone and that the two components act synergistically to give such effects.

FIG. 2*b* is an example of the data obtained from one bronchoconstricted rat exposed to FC-43 plus 5% by volume in air $CO_2$ mixture. The percent drop in Penh was 47% over the first 5 minutes and the effect was sustained for 12 minutes.

FIG. 3 shows that combining 20% $CO_2$ by volume in air with an aerosol of FC-43 results in a more prolonged bronchodilation (approximately 14 minutes) than was seen with 20% $CO_2$ in air alone (approximately 2 minutes).

EXAMPLE 3

Time Course of the Response to PFC and $CO_2$

In these experiments, a mixture of FC-43 and 20% $CO_2$ by volume in air was delivered as a single bolus over a 30 second period. To obtain the single bolus for delivery, the output of the Arcotech nebulizer was captured in two large (5 liter)

plastic bags, and the contents delivered to the rat in the exposure chamber over a 30 second period. Pulmonary function was recorded immediately afterward. The FC-43 concentration in the bolus was determined in a separate experiment to be about 39 mg/liter.

Figure 4A:
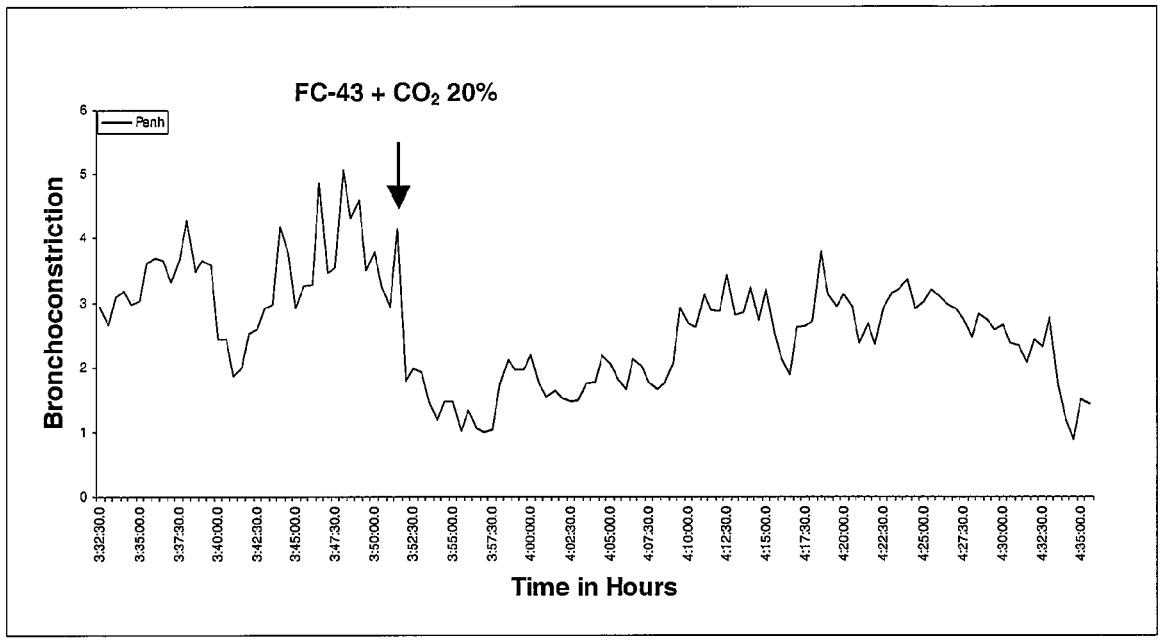
FIG. 4a is a graph showing the bronchodilatory effect of FC-43 and 20% $CO_2$ in air delivered as a single bolus over a 30 second period.

FIG. 4*a* shows the bronchodilatory effect of FC-43 and 20% $CO_2$ in air delivered as a single bolus over a 30 second period. There is an immediate bronchodilatory effect of about 75% that persists for about 15 minutes after cessation of the treatment.

Figure 4B:
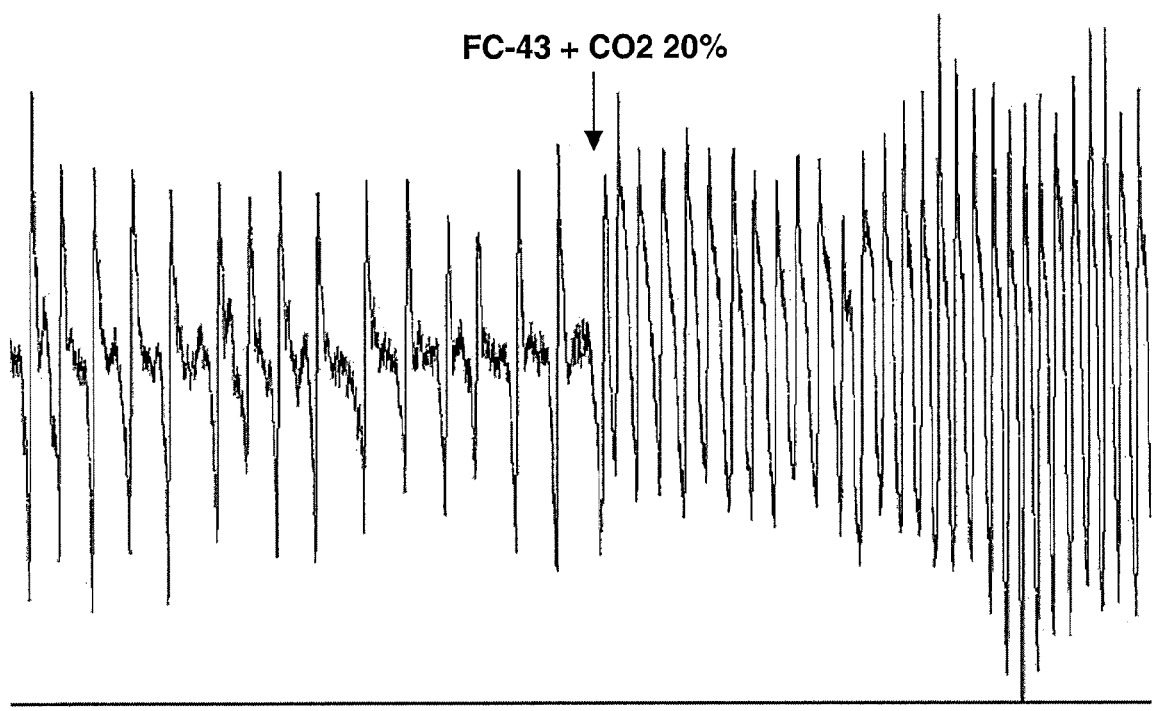
FIG. 4b is a graph showing the effect of the treatment shown in FIG. 4a on the wave form of the breaths immediately before and 30 seconds after treatment with FC-43 aerosol and 20% $CO_2$ in air.

FIG. 4*b* shows the effect of the treatment shown in FIG. 4*a* on the wave form of the breaths immediately before and 30 seconds after treatment with FC-43 aerosol and 20% $CO_2$ in air. The breathing wave before treatment shows an obstructive pattern with prolonged expiration. This returns to a normal pattern after 30 seconds of treatment.

EXAMPLE 4

Effect of Delivering a $\beta_2$ Agonist (Salbutamol) Along with a PFC/$CO_2$ Mixture FC-43 is placed in the Arcotech dual chamber jet nebulizer and driven by a gas mixture containing air and 5% $CO_2$ by volume. The concentration of FC-43 was determined as outlined above and averaged about 39 mg/liter. The treatment was delivered for 10 minutes. Two minutes after cessation of the first treatment, salbutamol (1 mg/ml) was delivered for 5 minutes using an ultrasonic nebulizer.

Figure 5A:
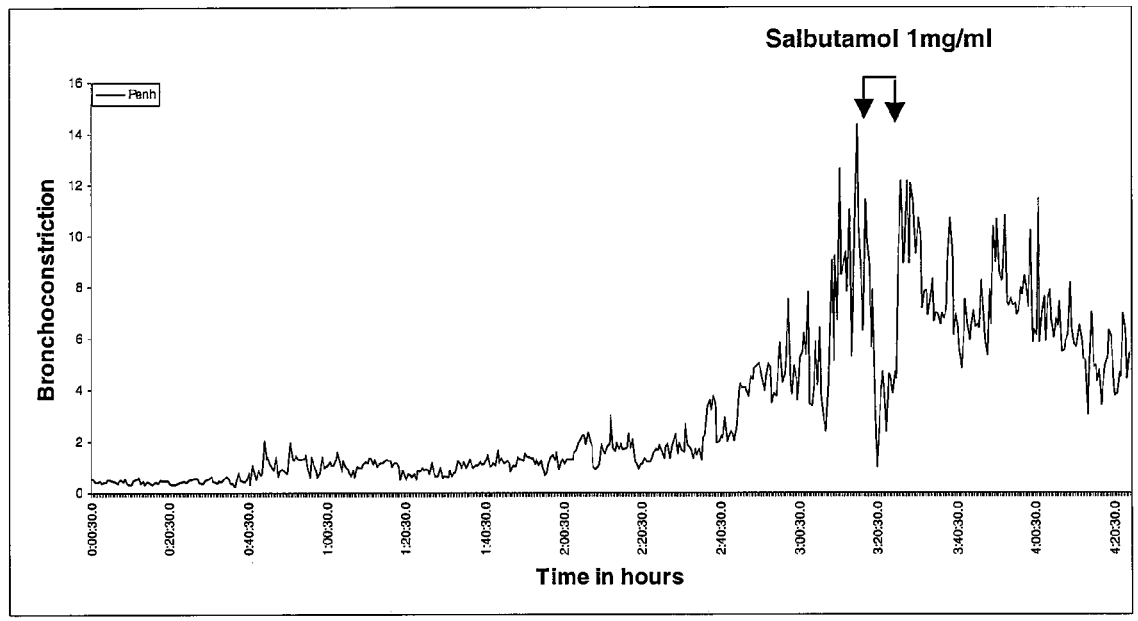
FIG. 5a is a graph showing the effects of salbutamol (1 mg/ml) alone on allergic bronchoconstriction in Brown Norway rats.
Figure 5B:
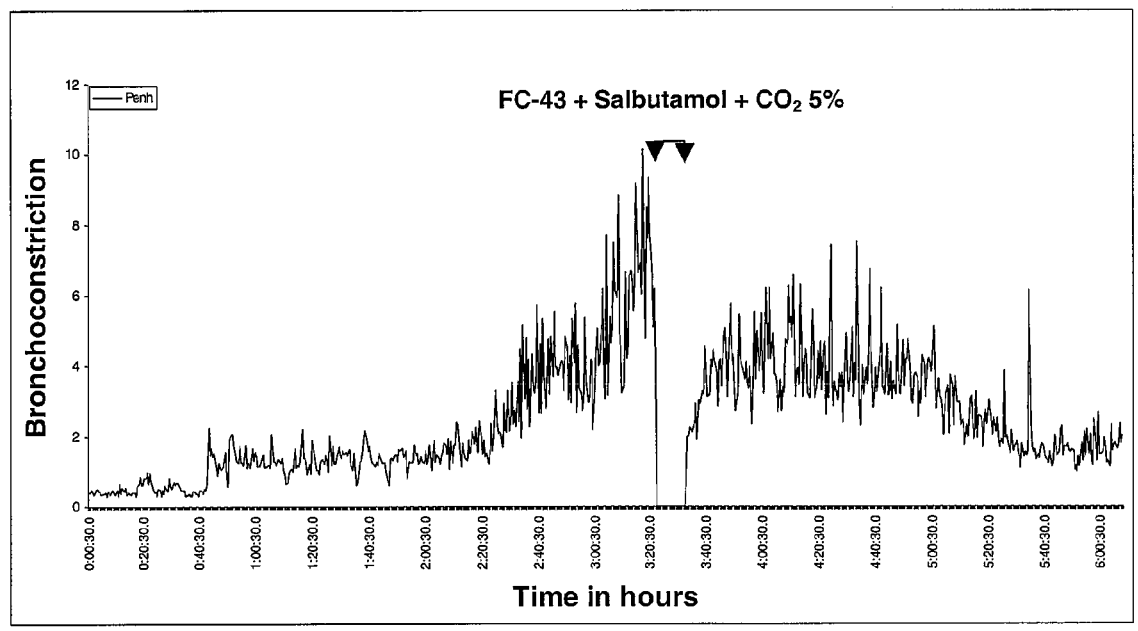
FIG. 5b is a graph showing the effects of FC-43, 5% carbon dioxide by volume in air, and salbutamol (1 mg/ml) on allergic bronchoconstriction in Brown Norway rats.
Figure 6A:
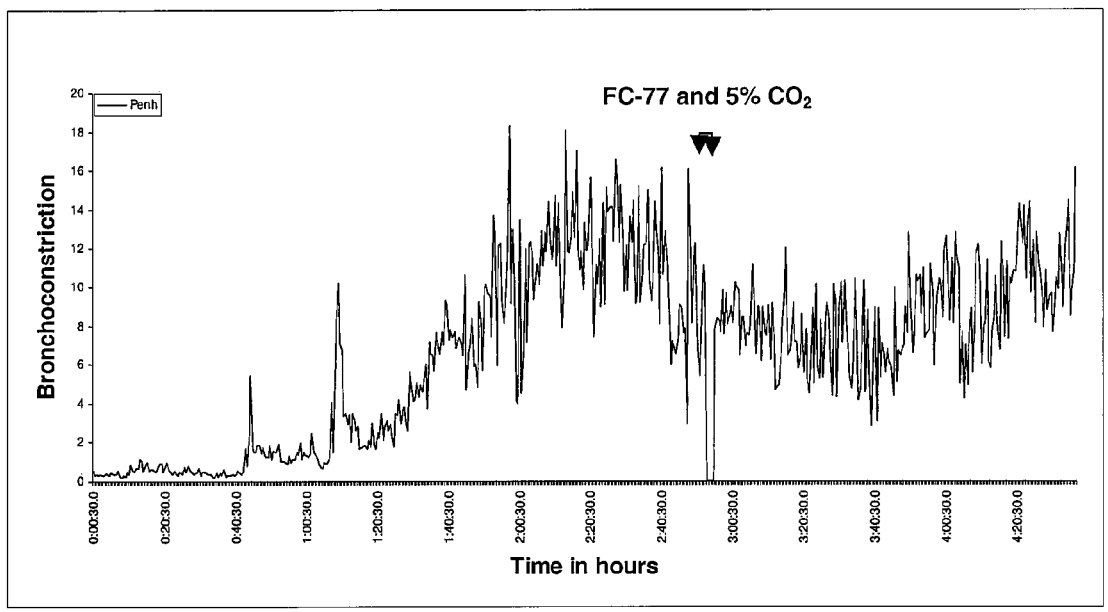
FIG. 6a is a graph showing the effect of the combination of FC-77 and 5% $CO_2$ by volume in air on allergic bronchoconstriction in Brown Norway rats.
Figure 6B:
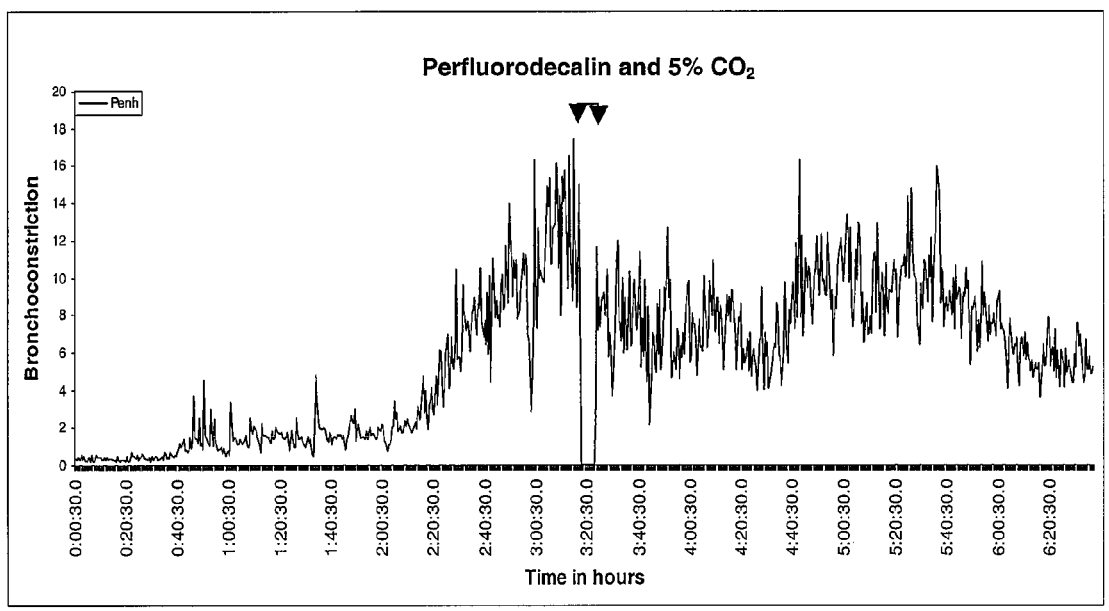
FIG. 6b is a graph showing the effect of the combination of perfluorodecalin and 5% $CO_2$ by volume in air on allergic bronchoconstriction in Brown Norway rats.
Figure 6C:
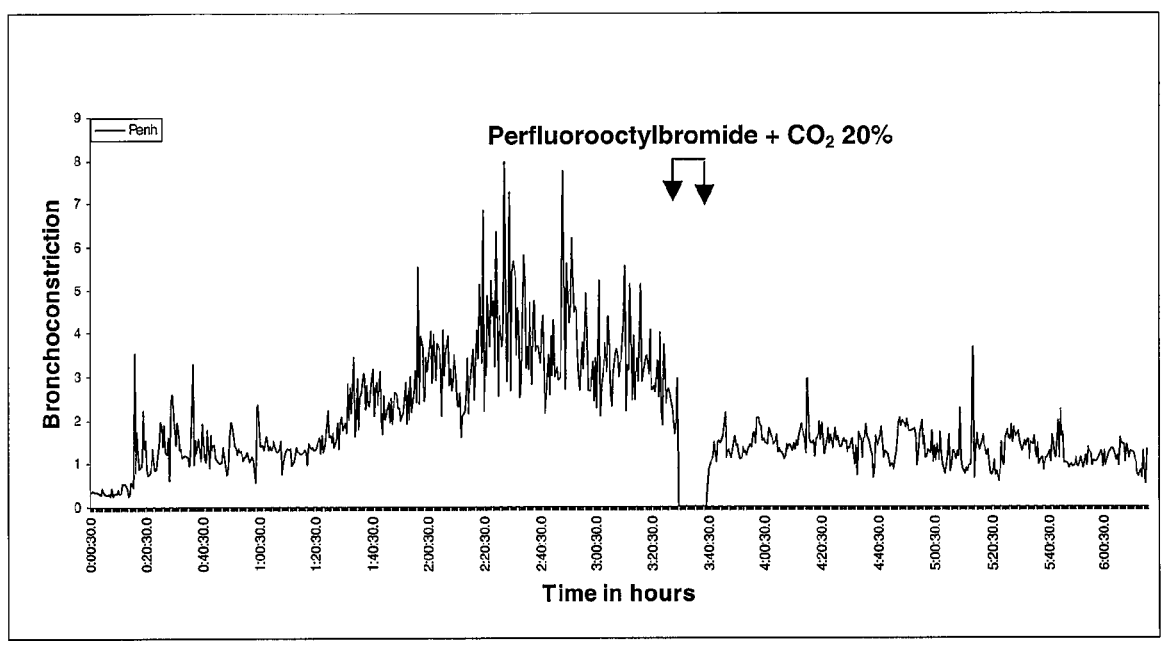
FIG. 6c is a graph showing the effect of the combination of perfluorooctylbromide and 20% $CO_2$ by volume in air on allergic bronchoconstriction in Brown Norway rats.
Figure 7A:
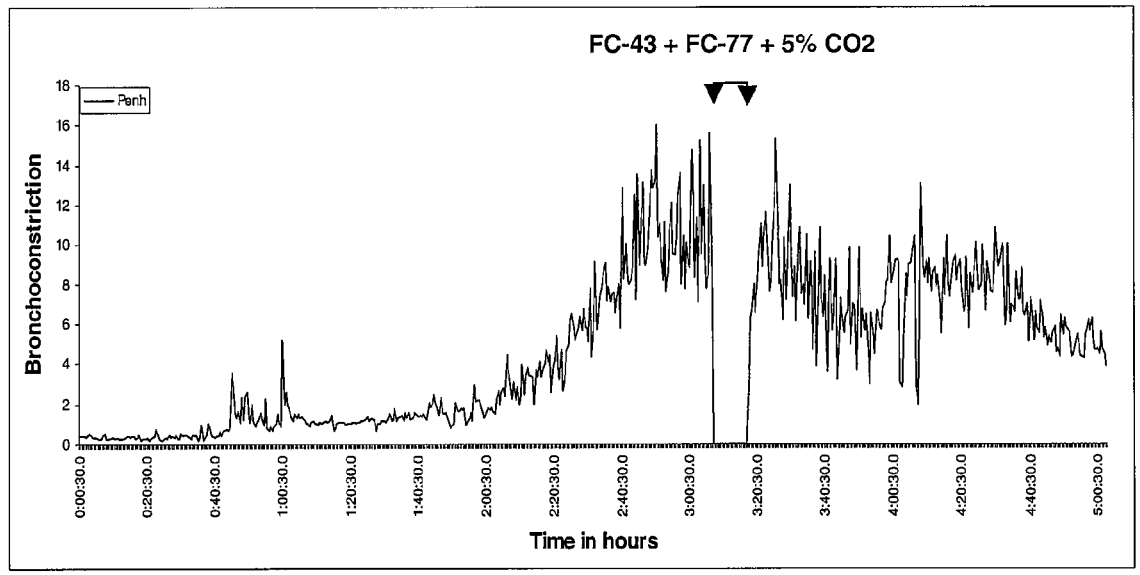
FIG. 7a is a graph showing the effect of the combination of FC-43, FC-77 and 5% $CO_2$ by volume in air on allergic bronchoconstriction in Brown Norway rats.
Figure 7B:
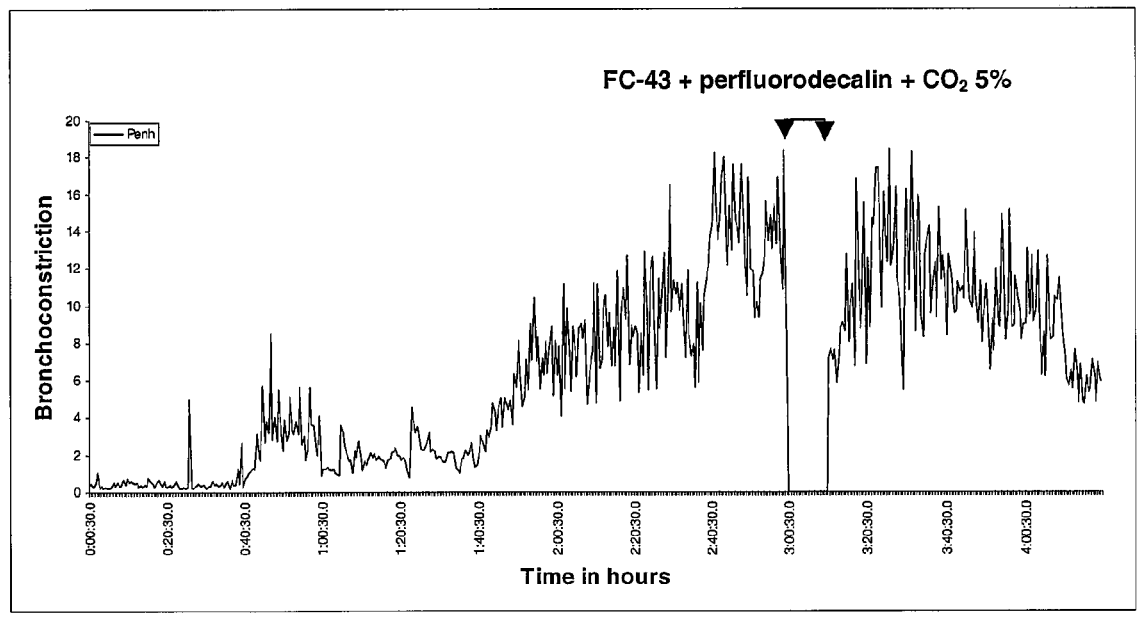
FIG. 7b is a graph showing the effect of the combination of FC-43, perfluorodecalin and 5% $CO_2$ by volume in air on allergic bronchoconstriction in Brown Norway rats.

FIG. 5*a* shows the bronchodilatory effect of salbutamol (1 mg/ml) on the asthmatic response. There is a rapid drop in Penh (approximately 60%), which in this experiment lasted for 5 minutes before returning to pretreatment levels. However, as shown in FIG. 5*b*, when 1 mg/ml salbutamol was given after PFC/$CO_2$ treatment the response is greater (approximately 70%) and was more prolonged and never returned to pre-treatment levels.

EXAMPLE 5

Effect of Combining $CO_2$ with Other PFCs (FC-77, Perfluorodecalin and Perfluorooctylbromide (PFOB))

FC-77 is placed in the Arcotech dual chamber jet nebulizer and driven by a gas mixture containing air and 5% $CO_2$ by volume. The treatment was delivered for 10 minutes. For technical reasons pulmonary function was evaluated immediately after cessation of the treatment.

Perfluorodecalin is placed in the Arcotech dual chamber jet nebulizer and driven by a gas mixture containing air and 5% $CO_2$ by volume. The treatment was delivered for 10 minutes. For technical reasons pulmonary function was evaluated immediately after cessation of the treatment.

Perfluorooctylbromide is placed in the Arcotech dual chamber jet nebulizer and driven by a gas mixture containing air and 20% $CO_2$ by volume. The treatment was delivered for 10 minutes. For technical reasons pulmonary function was evaluated immediately after cessation of the treatment.

FIG. 6*a* shows the bronchodilatory effect of the combination of FC-77 with 5% $CO_2$ in air on Penh. The combination results in a sustained drop in Penh of approximately 35% and that the effect on bronchodilation lasted for approximately 50 minutes.

FIG. 6*b* shows the bronchodilatory effect of the combination of perfluorodecalin with 5% $CO_2$ in air on Penh. The combination results in a sustained drop in Penh of approximately 50% and that the effect on bronchodilation lasted for about one (1) hour.

FIG. 6*c* shows the bronchodilatory effect of the combination of perfluorooctylbromide with 20% $CO_2$ in air on Penh. The combination results in a sustained drop in Penh of approximately 70% and that the effect on bronchodilation lasted for the duration of the experiment (2:20 hrs).

EXAMPLE 6

Effect of Combining Two PFCs with $CO_2$ in Air Mixture

A mixture of approximately equal amounts of FC-43 and FC-77 was placed in the Arcotech dual chamber jet nebulizer and driven by a gas mixture containing air and 5% $CO_2$ by volume. The treatment was delivered for 10 minutes. For technical reasons pulmonary function was evaluated immediately after cessation of the treatment.

A mixture of approximately equal amounts FC-43 and perfluorodecalin was placed in the Arcotech dual chamber jet nebulizer and driven by a gas mixture containing air and 5% $CO_2$ by volume. The treatment was delivered for 10 minutes. For technical reasons pulmonary function was evaluated immediately after cessation of the treatment.

FIG. 7*a* shows the bronchodilatory effect of a combination of FC-43 and FC-77 in a gas mixture containing 5% $CO_2$. The combination results in a drop in Penh of approximately 26% over 5 minutes after cessation of treatment, and was sustained for approximately 10 minutes. FIG. 7*b* shows the bronchodilatory effect of a combination of FC-43 and perfluorodecalin in a gas mixture containing 5% $CO_2$. The combination results in a drop in Penh of approximately 45% and was sustained for approximately 10 minutes.

The invention claimed is:

1. A method for treating a mammal suffering from a respiratory disease characterized by acute, intermittent or chronic obstruction of the airways of the lungs by dilating the airways, comprising delivering to the lungs of the mammal a therapeutically effective amount of a combination of a perfluorocarbon and a $CO_2$-containing gas mixture, wherein the combination exhibits therapeutic synergy in the dilation of the airways.

2. The method of claim 1, wherein the concentration of $CO_2$ in the $CO_2$-containing gas mixture is such that when the combination is delivered to the lungs the concentration of $CO_2$ in the lungs is at least 2% of the mammal's total lung capacity, wherein the total lung capacity comprises the fluid volume of the lung when fully inflated during normal breathing.

3. The method of claim 1, wherein the concentration of $CO_2$ in the $CO_2$-containing gas mixture is such that when the combination is delivered to the lungs the concentration of $CO_2$ in the lungs is about 2% to about 20% of the mammal's total lung capacity, wherein the total lung capacity comprises the fluid volume of the lung when fully inflated during normal breathing.

4. The method of claim 1, wherein the combination of perfluorocarbon and $CO_2$-containing gas mixture is delivered to the lungs as an aerosolized mixture.

5. The method of claim 1, wherein the combination of perfluorocarbon and $CO_2$-containing gas mixture is delivered to the lungs as a liquid bolus.

6. The method of claim 1, wherein the $CO_2$-containing gas mixture comprises oxygen and nitrogen.

7. The method of claim 6, wherein the concentration of oxygen is such that when the combination is delivered to the lungs the concentration of oxygen in the lungs is about 21% to about 80% of the mammal's total lung capacity, wherein the total lung capacity comprises the fluid volume of the lung when fully inflated during normal breathing.

8. The method of claim 6, wherein the concentration of oxygen is such that when the combination is delivered to the lungs the concentration of oxygen in the lungs is about 15% to about 21% of the mammal's total lung capacity, wherein the total lung capacity comprises the fluid volume of the lung when fully inflated during normal breathing.

9. The method of claim 1, wherein in the $CO_2$-containing gas mixture consists essentially of $CO_2$.

10. The method of claim 1, wherein concentration of perfluorocarbon is such that when the combination is delivered to the lungs, the concentration of perfluorocarbon in the lungs when the lungs are fully inflated during normal breathing is between about 1 mg/liter and about 500 mg/liter.

11. A method for treating a mammal suffering from a respiratory disease characterized by acute intermittent or chronic obstruction of the airways of the lungs, comprising separately delivering to the lungs of the mammal a therapeutically effective amount of a perfluorocarbon and a gas mixture having a therapeutically effective amount of $CO_2$.

12. The method of claim 11 further comprising delivering to the lungs a therapeutically effective amount of a suitable active agent.

13. The method of claim 12, wherein the active agent is an anti-inflammatory drug.

14. The method of claim 13, wherein the anti-inflammatory drug is a corticosteroid or cromolyn sodium.

15. The method of claim 12, wherein the active agent is a bronchodilator.

16. The method of claim 15, wherein the bronchodilator is selected from the group consisting of theophylline, beta-adrenergic agonists, and anticholinergics.

17. The method of claim 15, wherein the bronchodilator is salbutamol.

18. The method of claim 1 wherein the combination of the perfluorocarbon and $CO_2$-containing gas mixture is delivered to the lungs of a mammal by an inhaler device comprising:

a first chamber containing the perfluorocarbon;

a second chamber containing the $CO_2$-containing gas mixture; and a mechanism for releasing the perfluorocarbon and the $CO_2$-containing gas mixture to the lungs.

19. The method of claim 1, wherein the perfluorocarbon is selected from the group consisting of perfluoro-alkanes, perfluoroethers, perfluoro amines, perfluorodecalin, perfluorohexane, octafluoropropane, perfluoroperhydrophenanthrene, perfluorobutane, perfluorooctane, perefluoromethyldecalin, perfluorocarbons containing bromide, perfluorooctylbromide, perfluorodecalin, perfluorooctylethane, bis(perfluorobutyl)ethane, FC-43, FC-40, FC-5312, FC-77, FC-75, and combinations thereof.

20. The method of claim 1, wherein the perfluorocarbon is selected from the group consisting of FC-43, FC-77, perfluorodecalin, perfluorooctylbromide, and combinations thereof.

21. The method of claim 11, wherein the perfluorocarbon is selected from the group consisting of perfluoro-alkanes, perfluoroethers, perfluoro amines, perfluorodecalin, perfluorohexane, octafluoropropane, perfluoroperhydrophenanthrene, perfluorobutane, perfluorooctane, perefluoromethyldecalin, perfluorocarbons containing bromide, perfluorooctylbromide, perfluorodecalin, perfluorooctylethane, bis(perfluorobutyl)ethane, FC-43, FC-40, FC-5312, FC-77, FC-75, and combinations thereof.

22. The method of claim 11, wherein the perfluorocarbon is selected from the group consisting of FC-43, FC-77, perfluorodecalin, perfluorooctylbromide, and combinations thereof.

23. The method of claim 1 further comprising delivering to the lungs a therapeutically effective amount of a suitable active agent.

24. The method of claim 23, wherein the active agent is a bronchodilator.

25. The method of claim 24, wherein the bronchodilator is salbutamol.

26. The method of claim 1, wherein the perfluorocarbon is a liquid, aerosol or vapour.

* * * * *